United States Patent [19]

Friedman

[11] Patent Number: 4,924,070
[45] Date of Patent: May 8, 1990

[54] APPARATUS FOR CONTROLLED IRRADIATION

[76] Inventor: Joshua Friedman, 13 Fairfield Ct., Ridgefield, Conn. 06877

[21] Appl. No.: 392,157

[22] Filed: Aug. 10, 1989

[51] Int. Cl.$^5$ .............................................. H05B 1/00
[52] U.S. Cl. .................................. 219/346; 219/221; 219/227; 219/229; 219/230; 219/347
[58] Field of Search ............... 219/201, 220, 221, 222, 219/227, 229, 230, 339, 342, 346, 347, 349, 366-371, 373, 374

[56] References Cited

U.S. PATENT DOCUMENTS

| | | | |
|---|---|---|---|
| 2,364,730 | 12/1944 | Leskin | 219/346 |
| 3,242,314 | 3/1966 | Eckles | 219/347 |
| 3,427,433 | 2/1969 | Foreman | 219/349 |
| 3,813,514 | 5/1974 | Canty | 219/347 |
| 3,864,547 | 2/1975 | Ray | 219/346 |
| 4,009,382 | 2/1977 | Nath | 219/349 |
| 4,079,104 | 3/1978 | Dickson | 219/349 |

Primary Examiner—Bruce A. Reynolds
Assistant Examiner—Leon K. Fuller
Attorney, Agent, or Firm—Eugene Lieberstein

[57] ABSTRACT

Apparatus for supplying light and heat of variable intensity to a photocurable dental material. The apparatus includes a source of light, a reflector, a filter assembly, a light guide and an electrical fan. The heat is generated from the light source and is controllably directed by an arrangement of louvers with a manually adjustable lever through a passageway surrounding the light guide to the operatory site.

9 Claims, 2 Drawing Sheets

APPARATUS FOR CONTROLLED IRRADIATION

FIELD OF THE INVENTION

This invention relates to apparatus for irradiating photocurable dental materials with both light and heat and with the supply of heat being variable.

BACKGROUND OF THE INVENTION

Polymerizable dental materials capable of being cured by exposure to high intensity light in a short time interval have become very popular. Commercially available photocurable materials are formulated to be cured by exposure to ultraviolet radiation in the spectral range between 300 to 400 nm and/or by exposure to visible light in the spectral range of between 400 to 500 nm. The light source is, in general, positioned as close to the point of application as is practical, so as to provide high intensity light directly to the restoration without the use of long fiber-optic light guides. This technique is currently used to deliver the maximum amount of optical power to the dental restorative material at the operatory site independently of the light assembly used It has been discovered that by supplementing the source of light with a source of heat, the physical properties of light-cured dental resins can be enhanced. The supplemental heat can be applied either during or after the curing process It has also been demonstrated that the bond strength of the cured dental materials to adjacent tooth structure can be significantly increased by curing these materials with a combined application of heat and light, as well as diametral tensile strength and surface hardness. The apparatus of the present invention provides a source for generating light over a preselected spectral range to effect polymerization of the dental material, in combination with a controlled variable source of heat, in the form of hot air, for supplementing the light radiation with a supply of heat during the light curing process in order to enhance the physical properties of the dental material. The physical properties which are susceptible to the present invention include the surface hardness, diametral tensile strength, and the flexure strength, as well as the shear strength to tooth structure.

SUMMARY OF THE INVENTION

Apparatus for irradiating photocurable dental material comprising:

a lamp for generating radiant energy;

reflecting means for reflecting energy emitted from said lamp to a desired focal point;

guide means for transmitting light reflected by said reflecting means along a predetermined direction to a site external of said Apparatus;

means for channeling heated ambient air generated by said lamp to cause it to flow along a predetermined path; and means for diverting a controlled amount of said heated ambient air from said predetermined path into said predetermined direction for simultaneously applying heat and light to said dental restoration.

BRIEF DESCRIPTION OF THE DRAWING

Other advantages of the invention not heretofore described will become apparent from the following detailed description of the invention when read in conjunction with the drawings of which.

DESCRIPTION OF THE PREFERRED EMBODIMENT

Figure 1:
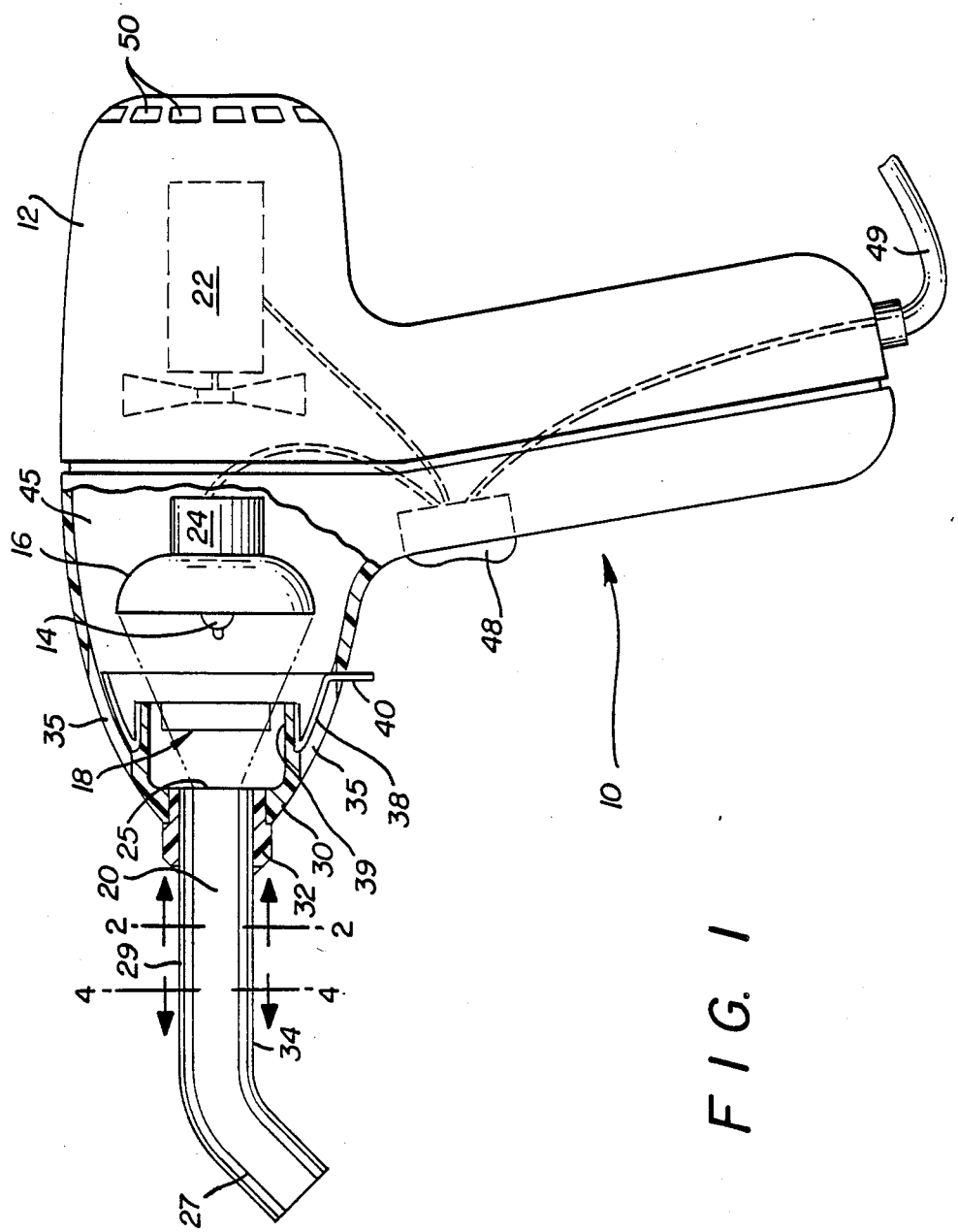
FIG. 1 is a longitudinal sectional view of a hand-held heat-and-light-transmitting assembly in accordance with the present invention.

The light-and-heat-transmitting assembly (10), as shown in FIG. 1, includes a housing (12) containing a source of radiant energy, such as a halogen lamp, (14), a reflector (16) for the lamp (14), a suitable filter or filter assembly (18), an optical guide (20), and an electrical fan (22).

The lamp (14) is mounted in a lamp socket (24) for generating energy over a predetermined spectral region. The lamp (14) may be selected of the tungsten/halogen type or of the mercury vapor, short-arc xenon, or metal halide type, dependent upon the desired spectral bandwidth of radiant energy. The filter assembly (18) is spaced apart from the lamp (14) in the position adjacent the proximal end (25) of the guide (20) along the optic axis for filtering light energy reflected from the reflector (16). The reflector (16) has an elliptical shape and is mounted behind the lamp (14) for reflecting and focusing light energy generated from the lamp (14) into the filter assembly (18). The filter assembly (18) may represent a single or multiple filter arrangement for passing radiant energy of suitable wavelength into the optical guide (20). The optical guide (20) is a glass, quartz or plastic fiber optic rod or other light-conducting medium of any preferred length. Generally, the optic guide (20) will be no more than 3 or 4 inches long, with a contoured tip (27) at the distal end thereof.

The optic light guide (20) is mounted in a coaxial tube (29) which is held in the nose cone (30) of the housing (12) by a bushing (32). The tube (29) surrounds the light guide (20) to provide an annular passage (34) between the tube (29) and the optic light guide (20) for the transmission of heat, as will be explained hereafter in greater detail.

Figure 2:
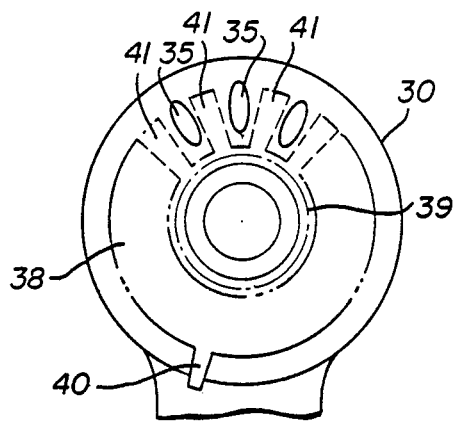
FIG. 2 is a front view of the heat-and-light source of FIG. 1 taken along the lines 2—2 of FIG. 1.
Figure 3:
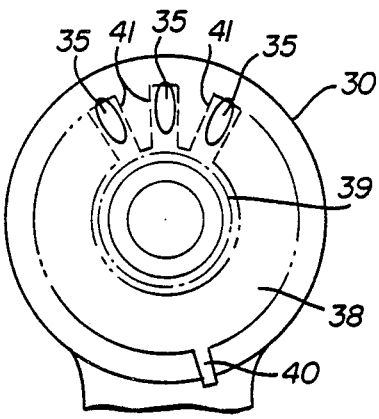
FIG. 3 is a view similar to FIG. 2 with the operational control lever adjusted from the normally open position shown in FIG. 2 to the fully closed position.

The nose cone (30) of the housing (12), as more clearly shown in FIGS. 2 and 3, includes a plurality of ventilation holes (35), which are annularly arranged about the nose cone (30) for drawing or exhausting fresh air from the housing (12), dependent upon the direction of rotation of the electrical fan (22). A manually adjustable louver (38) is mounted over the nose cone (30) and supported by a bushing (39) extending from the nose cone (30). The manually adjustable louver (38) has an operating lever (40) for adjusting the position of the vanes (41) relative to the ventilation holes (35) in order to regulate the size of the opening through the ventilation holes (35).

Air in the interior space (45) of the housing (12) is heated by the lamp (14), which typically has a power of between 25 and 150 watts. The electrical fan (22) is in an electrical circuit with a manually controlled operating switch (48), the lamp socket (24), and a power supply (not shown) through an electrical cable (49). The manually controlled operating switch (48) is actuable by the thumb or forefinger for switching on the lamp (14) and fan (22). The switch (48) may be a three-position switch permitting the fan direction to be reversed in two separate modes of operation and an "off" position. Alternatively, a push button switch with a logic sequence may be used to control the fan direction and lamp function to achieve the same effect.

During normal operation, the manually adjustable louver (38) is in the position shown in FIG. 2, with the ventilation holes (35) exposed to the atmosphere. Air is drawn in through the ventilation holes (35), with the fan (22) operated to exhaust the ambient air heated by the lamp (14) through the ventilation holes (50) in the housing (12).

When the operator wishes to direct heat and light at the dental restoration, the direction of the fan (22) is reversed by operation of the switch (48) so that air is now drawn into the housing (12) from the ventilation holes (50). The amount of heat directed at the restoration is controlled by turning the operating lever (40) of the adjustable louver (38). In FIG. 3, the vanes (41) are shown closing off the ventilation holes (35), thereby directing all of the heated ambient air from the housing (12) into the air channel (34) between the tube (29) and the optic light guide (20). By adjustment of the operating lever (40), the volume and temperature of warm air supplied through the air channel (34) to the restorative dental material can be varied. The temperature may also be varied by using a fan with adjustable speed.

Figure 4B:
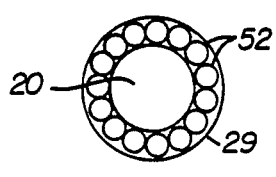
FIG. 4(b) is a sectional view similar to FIG. 4a showing an alternate arrangement for transmitting light and heat.
Figure 4A:
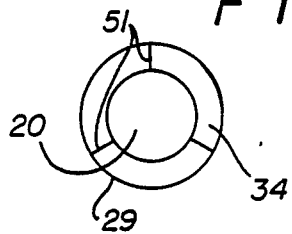
FIG. 4(a) a sectional view taken along the lines 4—4 of FIG. 1.
Figure 4C:
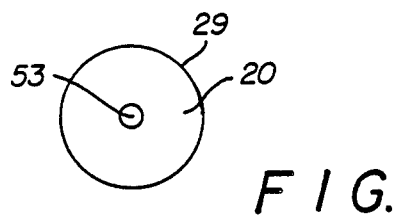
FIG. 4(c) is another sectional view similar to FIG. 4(a) showing another embodiment for transmitting light and heat.

The air channel (34) may represent an annular passageway, as shown in FIG. 4(a), with ribs (51) or a plurality of passages formed by a multiple number of tubes (52) embedded in the space (34). The tubes (52) may be composed from any material, including glass, metal, or plastic. In both of the arrangements of FIGS. 4(a) and 4(b), the optic light guide (20) represents the center core of a coaxial construction with the heated air passageway (34) surrounding the light beam. In the embodiment of FIG. 4(c), the center core is a relatively small diameter hollow pipe (53) through which heated air is directed. A fiber optic bundle (20) surrounds the hot air pipe (53) for transmitting light around the hot air flow.

I claim:

1. Apparatus for irradiating photocurable dental material comprising:
   a lamp for generating radiant energy;
   reflecting means for reflecting energy emitted from said lamp to a desired focal point;
   optic guide means for transmitting light reflected by said reflecting means along a predetermined direction to a photocurable material at a site external of said Apparatus;
   means for channeling heated ambient air generated by said lamp to cause it to flow along a predetermined path; and
   means for diverting a controlled amount of said heated ambient air from said predetermined path into said predetermined direction for applying heat to said photocurable material.

2. Apparatus, as defined in claim 1, wherein said heat and light are simultaneously applied.

3. Apparatus, as defined in claim 2, wherein said means for diverting said heated air is adjustable for controlling the temperature of said heated ambient air.

4. Apparatus, as defined in claim 3, further comprising conduit means for directing the flow of said diverted heated air along a path which is coaxial to said optic guide means.

5. Apparatus, as defined in claim 4, wherein said diversion means for said heated air is an adjustable louver.

6. Apparatus, as defined in claim 5, further comprising a housing for said apparatus;
   an electric fan for channeling said heated ambient air in said housing;
   a first set of ventilation holes for drawing air into said housing;
   a second set of ventilation holes for exhausting air from said housing with said adjustable louver positioned adjacent said second set of ventilation holes so as to adjust the flow of heated air passed through said conduit means.

7. Apparatus, as defined in claim 6, wherein said conduit means surrounds said optic guide means.

8. Apparatus, as defined in claim 7, further comprising a plurality of tubes surrounding said optic guide means.

9. Apparatus, as defined in claim 6, wherein said optic guide means surrounds said heated air conduit means.

* * * * *